(12) United States Patent
Gourlay et al.

(10) Patent No.: US 10,939,836 B2
(45) Date of Patent: Mar. 9, 2021

(54) MODULAR LIGHT PANEL HAVING LIGHT SOURCES AND ENVIRONEMENTAL SENSOR UNITS

(71) Applicant: DESIGN LED PRODUCTS LIMITED, West Lothian (GB)

(72) Inventors: James Gourlay, West Lothian (GB); Stuart Bain, West Lothian (GB); Derek Peden, West Lothian (GB)

(73) Assignee: DESIGN LED PRODUCTS LIMITED, Lothian (GB)

( * ) Notice: Subject to any disclaimer, the term of this patent is extended or adjusted under 35 U.S.C. 154(b) by 0 days.

(21) Appl. No.: 16/097,547

(22) PCT Filed: May 2, 2017

(86) PCT No.: PCT/GB2017/051219
§ 371 (c)(1),
(2) Date: Oct. 29, 2018

(87) PCT Pub. No.: WO2017/187204
PCT Pub. Date: Nov. 2, 2017

(65) Prior Publication Data
US 2019/0150766 A1  May 23, 2019

(30) Foreign Application Priority Data
Apr. 29, 2016 (GB) .................................... 1607603

(51) Int. Cl.
*F21V 23/04* (2006.01)
*A61B 5/024* (2006.01)
(Continued)

(52) U.S. Cl.
CPC ........ *A61B 5/02427* (2013.01); *A61B 5/6891* (2013.01); *F21S 8/026* (2013.01);
(Continued)

(58) Field of Classification Search
CPC ............... F21V 23/005; F21V 23/0442; F21V 23/0464; F21V 23/0471; F21V 23/003;
(Continued)

(56) References Cited

U.S. PATENT DOCUMENTS 7,187,141 B2 * 3/2007 Mueller .................. F21K 9/232
315/362
7,604,377 B2 * 10/2009 Yu ........................ H05K 1/0274
362/249.02
(Continued)

FOREIGN PATENT DOCUMENTS

CN  101523634 A   9/2009
CN  104145159 A   11/2014
(Continued)

OTHER PUBLICATIONS

International Search Report and Written Opinion dated Jul. 6, 2017.
Chinese Office Action dated Mar. 3, 2020.

*Primary Examiner* — Ismael Negron
(74) *Attorney, Agent, or Firm* — FisherBroyles, LLP

(57) ABSTRACT

A modular light panel includes a transparent base substrate, an array of light sources, at least one environment sensor unit mounted on the base substrate, and a transparent protecting layer encapsulating the light sources and the environment sensor unit(s). The refractive index of the transparent protecting layer is equal or less than that of the base substrate. The modular light panel might also include a wireless communication module.

39 Claims, 4 Drawing Sheets

(51) Int. Cl.
*F21S 8/02* (2006.01)
*A61B 5/00* (2006.01)
*F21V 3/04* (2018.01)
*F21V 33/00* (2006.01)
*G01K 3/14* (2006.01)
*F21Y 115/10* (2016.01)
*F21Y 109/00* (2016.01)
*F21W 131/208* (2006.01)
*F21Y 105/10* (2016.01)
*F21W 131/301* (2006.01)

(52) U.S. Cl.
CPC ............ *F21V 3/049* (2013.01); *F21V 23/045* (2013.01); *F21V 23/0435* (2013.01); *F21V 23/0464* (2013.01); *F21V 23/0471* (2013.01); *F21V 23/0478* (2013.01); *F21V 33/0012* (2013.01); *F21V 33/0076* (2013.01); *G01K 3/14* (2013.01); *A61B 2560/0242* (2013.01); *A61B 2562/029* (2013.01); *A61B 2562/0247* (2013.01); *F21W 2131/208* (2013.01); *F21W 2131/301* (2013.01); *F21Y 2105/10* (2016.08); *F21Y 2109/00* (2016.08); *F21Y 2115/10* (2016.08)

(58) Field of Classification Search
CPC ............... F21V 23/004; F21Y 2105/16; F21Y 2105/10; F21Y 2115/10
See application file for complete search history.

(56) References Cited

U.S. PATENT DOCUMENTS

| | | | | |
|---|---|---|---|---|
| 8,044,415 | B2* | 10/2011 | Messere | B32B 17/10174 257/88 |
| 8,246,200 | B2* | 8/2012 | Lai | F21V 5/007 315/192 |
| 8,568,010 | B2* | 10/2013 | Ashdown | F21S 8/06 359/598 |
| 8,944,637 | B2* | 2/2015 | Spiro | F16L 3/06 362/294 |
| 9,052,069 | B2* | 6/2015 | Romas | F21V 23/005 |
| 9,689,555 | B2* | 6/2017 | Baaijens | F21S 8/026 |
| 9,700,641 | B2* | 7/2017 | Hawkins | A61N 5/06 |
| 9,799,811 | B2* | 10/2017 | Maki | H01L 25/0753 |
| 2009/0251917 | A1 | 10/2009 | Wollner et al. | |
| 2009/0267540 | A1 | 10/2009 | Chemel et al. | |
| 2010/0289428 | A1* | 11/2010 | Frazier | F21V 23/0442 315/294 |
| 2011/0193105 | A1 | 8/2011 | Lerman et al. | |
| 2011/0198026 | A1 | 8/2011 | Gourlay | |
| 2011/0254554 | A1 | 10/2011 | Harbers | |
| 2012/0002438 | A1 | 1/2012 | Gourlay | |
| 2012/0195032 | A1* | 8/2012 | Shew | H02J 9/065 362/183 |
| 2012/0235579 | A1 | 9/2012 | Chemel et al. | |
| 2012/0268963 | A1 | 10/2012 | Gourlay | |
| 2012/0287631 | A1 | 11/2012 | Sheng | |
| 2013/0094225 | A1 | 4/2013 | Leichner | |
| 2013/0148357 | A1 | 6/2013 | Johnston et al. | |
| 2013/0294050 | A1 | 11/2013 | Lee et al. | |
| 2013/0327966 | A1 | 12/2013 | Fidler et al. | |
| 2014/0133137 | A1 | 5/2014 | Kiss | |
| 2014/0168610 | A1 | 6/2014 | Spaulding et al. | |
| 2014/0254829 | A1 | 9/2014 | Wang et al. | |
| 2014/0268678 | A1* | 9/2014 | Potucek | F21V 23/0471 362/101 |
| 2014/0292194 | A1 | 10/2014 | Sagal et al. | |
| 2015/0098709 | A1 | 4/2015 | Breuer et al. | |
| 2015/0311406 | A1 | 10/2015 | Lange et al. | |
| 2015/0318430 | A1 | 11/2015 | Schicktanz et al. | |
| 2015/0330834 | A1 | 11/2015 | Griffin et al. | |
| 2015/0338029 | A1 | 11/2015 | Diekmann et al. | |
| 2015/0338077 | A1 | 11/2015 | Johnson | |
| 2015/0371585 | A1 | 12/2015 | Bower et al. | |
| 2015/0377479 | A1 | 12/2015 | Pescod et al. | |

FOREIGN PATENT DOCUMENTS

| | | |
|---|---|---|
| CN | 105114830 A | 12/2015 |
| CN | 204943108 U | 1/2016 |
| CN | WO2016/015499 A1 | 2/2016 |
| CN | 205191377 U | 4/2016 |
| EP | 0354468 A2 | 8/1989 |
| GB | 2448564 A | 10/2008 |
| GB | 2498347 A | 7/2013 |
| GB | 2500055 A | 9/2013 |
| KR | 2012/0117389 A | 10/2012 |
| WO | WO2012/160390 A1 | 11/2012 |
| WO | WO2013132271 A1 | 9/2013 |
| WO | WO2015/165317 A1 | 11/2015 |
| WO | WO2015/178254 A1 | 11/2015 |
| WO | WO2015177762 A2 | 11/2015 |

* cited by examiner

MODULAR LIGHT PANEL HAVING LIGHT SOURCES AND ENVIRONEMENTAL SENSOR UNITS

This application is the U.S. National Stage of International Application No. PCT/GB2017/051219, which was filed on May 2, 2017. This application also claims the benefit of the filing date of GB patent application No. 1607603.6, which was filed on Apr. 29, 2016. The contents of both of those applications are hereby incorporated by reference in its entirety.

The present invention relates to the field of lighting and in particular to a modular light panel that incorporates one or more environment sensors so as to provide the modular light panel with increased functionality in response to a volume illuminated by the device.

BACKGROUND TO THE INVENTION

Recently there has been a desire for the increased control of lighting systems, commonly referred to as "Smart Lighting". Primarily the development of these systems has been driven by a desire for increased energy efficiency to satisfy building codes, or comply with green building and energy conservation programs. Typically, these systems include high efficiency fixtures and central automated controls that make adjustments based on conditions such as occupancy or daylight availability.

In this context, the term lighting refers to the deliberate application of light to achieve some aesthetic or practical effect. It includes task lighting (i.e. increasing illuminance or varying contrast to better accomplish a specific activity), accent lighting (i.e. the focussing of light on a particular area or object), and general lighting.

These so called "Smart Lighting" systems are typically formed from modular lighting panels of the type disclosed with US patent publication number US 2014/0133137 and international patent publication number WO 2012/160390. Each modular light panel comprises a printed circuit board (PCB) upon which is mounted one or more light sources and an additional sensor unit employed for example to detect a change in temperature or light levels in the vicinity of the light panel and or the presence of an object (e.g. a person) within a predetermined proximity of the light panel. Electrical wiring on the PCB connects the light sources and the additional sensors to an electrical connector. This arrangement permits mechanical and electrical serial connection of multiple modular lighting panels.

A disadvantage of these systems relates to reduced light outputs due to the absorption of light generated by the light sources by the PCBs. This is exacerbated be the introduction of the additional sensor units which themselves act to absorb light. In addition, the additional sensor units also act to disrupt the propagation of light laterally across the device thus reducing the overall uniformity of the output light form the device. This is obviously undesirable for many lighting systems e.g. room lighting.

SUMMARY OF THE INVENTION

It is therefore an object of an aspect of the present invention to provide an alternative modular light panel that obviates or at least mitigates the foregoing disadvantages of the modular light panels known in the art.

It is a further object of an aspect of the present invention to provide an alternative modular light panel that exhibits increased functionality when compared to those modular light panels known in the art.

The terms "transparent" and "opaque" employed throughout the following description relate to the optical properties of particular components of the device relative to the wavelength of the light generated by the incorporated light sources.

According to a first aspect of the present invention there is provided a modular light panel comprising:
a transparent base substrate having a first refractive index, upon a first surface of which are mounted an array of one or more light sources;
a transparent protecting layer, having a second refractive index that is less than or equal to the first refractive index, arranged to encapsulate the array of one or more light sources upon the first surface and form a composite structure with the transparent base substrate for guiding light produced by the one or more light sources within the composite structure;
wherein the modular light panel further comprises one or more environment sensor units located on the first surface to measure one or more physical properties of a volume illuminated by the array of one or more light sources.

In the context of the present application the term environment sensor refers to a sensor capable of measuring one or more physical properties of a surrounding environment inclusive of ambient illumination, ambient temperature, ambient pressure, and ambient fluid composition (e.g. humidity and or the presence of air pollutants such as smoke, carbon monoxide or carbon dioxide in the surrounding air).

The array of one or more light sources may be located centrally upon the first surface. In this embodiment, the one or more environment sensor units may be located around the perimeter of the array of one or more light sources.

Preferably the transparent protecting layer also encapsulates the one or more environment sensor units upon the first surface. In this embodiment, one or more apertures may be located within the transparent protecting layer to provide a means for fluid communication place between the one or more environment sensor units and the volume illuminated by the array of one or more light sources.

The one or more environment sensor units may comprise a thermometer arranged to measure the ambient temperature of the volume illuminated by the array of one or more light sources.

The one or more environment sensor units may comprise a photodetector arranged to measure the ambient light levels of the volume illuminated by the array of one or more light sources.

The one or more environment sensor units may comprise a pressure sensor arranged to measure the ambient pressure of the volume illuminated by the array of one or more light sources.

The one or more environment sensor units may comprise a hygrometer arranged to measure the ambient humidity of the volume illuminated by the array of one or more light sources.

The one or more environment sensor units may comprise a smoke detector arranged to detect the presence of smoke within the volume illuminated by the array of one or more light sources.

The one or more environment sensor units may comprise a gas detector arranged to detect the presence of one or more gases within the volume illuminated by the array of one or more light sources e.g. carbon monoxide or carbon dioxide.

Optionally the modular lighting panel further comprises a motion sensor that provides a means for detecting movement within the volume illuminated by the array of one or more light sources. In this way, the array of lights can be automatically turned on when movement is detected within the volume illuminated by the array of one or more light source. The motion sensor is preferably mounted upon the first surface.

Optionally the modular lighting panel further comprises an image capture device (e.g. a camera) that provides a means for imaging the volume illuminated by the array of one or more light sources. The image capture device is preferably mounted upon the first surface.

Optionally the modular lighting panel further comprises a wireless communication module that provided a means for automated control of the functionality of the device. The wireless communication module may provide a means for configuring the modular lighting panel to communicate with the Internet of Things (IoT). The wireless communication module is preferably mounted upon the first surface. The wireless communication module may comprise a WiFi, LiFi or Bluetooth communication module. The wireless communication module may comprise an inductive antenna.

Optionally the modular lighting panel further comprises a computer processing unit (CPU) that provides a means for automatically controlling one or more of the other components of the modular lighting panel. The CPU is preferably mounted upon the first surface.

Optionally the modular lighting panel further comprises a thermostat controller to provide a means for regulating the temperature within the volume illuminated by the array of one or more light sources. The CPU may be employed as the thermostat controller.

The modular lighting panel preferably comprises electrical tracking located on the first surface that provides a means for supply power to the array of one or more light sources and the one or more environment sensor units.

The electrical tracking may also provide a means for supplying power to the motion sensor. The electrical tracking may also provide a means for supplying power to the wireless communication module. The electrical tracking may also provide a means for supplying power to the CPU.

Power for the modular lighting panel may be provided by a dedicated power source located within the modular lighting panel.

Alternatively, or additionally, the electrical tracking may be electrically connected to one or more connecting means located around the perimeter of the modular lighting panel.

Most preferably the connecting means are universal connecting means. In this way, there is no dedicated input or output connecting means for the modular lighting panel and so multiple modular lighting panels can be joined universally, by any of the connecting means so as to provide a highly flexible lighting system.

The connecting means may be connected to an external power source e.g. mains power.

Most preferably the modular lighting panel further comprises one or more scattering structures arranged to direct light generated by the array of one or more light sources towards an exit surface of the modular lighting panel. The one or more scattering structures may be located on a second surface of the transparent base substrate the second surface being opposite to the first surface.

Optionally the modular lighting panel further comprises a reflective layer formed behind the second surface to further assist in directing light generated by the array of one or more light sources towards the exit surface of the modular lighting panel.

Optionally the one or more environment sensor units are formed on an organic layer. This embodiment has the advantage that the modular lighting panel is simpler to manufacture since all of the environment sensor units are provided upon a single preformed component. The organic layer may comprise a transparent polymer sheet, such as polyester or polycarbonate, having a refractive index $n_o$.

The array of one or more light sources may also be formed on the organic layer. Similarly, one or more of the motion sensor, the wireless communication module and the CPU may also be formed on the organic layer.

According to a second aspect of the present invention there is provided a light panel comprising two or more modular lighting panels in accordance with the first aspect of the present invention.

The light panel may form a ceiling section of a room.

Embodiments of the second aspect of the invention may comprise features to implement the preferred or optional features of the first aspect of the invention or vice versa.

According to a third aspect of the present invention there is provided an arm rest for a chair comprising a modular lighting panel in accordance with the first aspect of the present invention.

The arm rest may further comprise a pulse measuring meter located within the modular lighting panel.

Embodiments of the third aspect of the invention may comprise features to implement the preferred or optional features of the first or second aspects of the invention or vice versa.

According to a fourth aspect of the present invention there is provided a method of thermally mapping the temperature of the room the method comprising deploying two or more modular lighting panels in accordance with the first aspect of the present invention within a ceiling area of the room.

Embodiments of the fourth aspect of the invention may comprise features to implement the preferred or optional features of the first or second aspects of the invention or vice versa.

According to a fifth aspect of the present invention there is provided a modular light panel comprising:
a transparent base substrate having a first refractive index, upon a first surface of which are mounted an array of one or more light sources;
a transparent protecting layer, having a second refractive index that is less than or equal to the first refractive index, arranged to encapsulate the array of one or more light sources upon the first surface and form a composite structure with the transparent base substrate for guiding light produced by the one or more light sources within the composite structure;
wherein the modular light panel further comprises a wireless communication module that provided a means for automated control of the functionality of one or more devices connected to the modular light panel.

The wireless communication module may provide a means for configuring the modular lighting panel to communicate with the Internet of Things (IoT). The wireless communication module is preferably mounted upon the first surface. The wireless communication module may comprise a WiFi, LiFi or Bluetooth communication module The wireless communication module may comprise an inductive antenna.

The one or more devices connected to the modular light panel may comprises one or more environment sensor units located on the first surface to measure one or more physical properties of a volume illuminated by the array of one or more light sources.

Optionally, the one or more devices may comprise one or more devices located externally of the modular light panel.

Embodiments of the fifth aspect of the invention may comprise features to implement the preferred or optional features of the first to fourth aspects of the invention or vice versa.

BRIEF DESCRIPTION OF THE DRAWINGS

There will now be described, by way of example only, various embodiments of the invention with reference to the drawings, of which.

Figure 1:
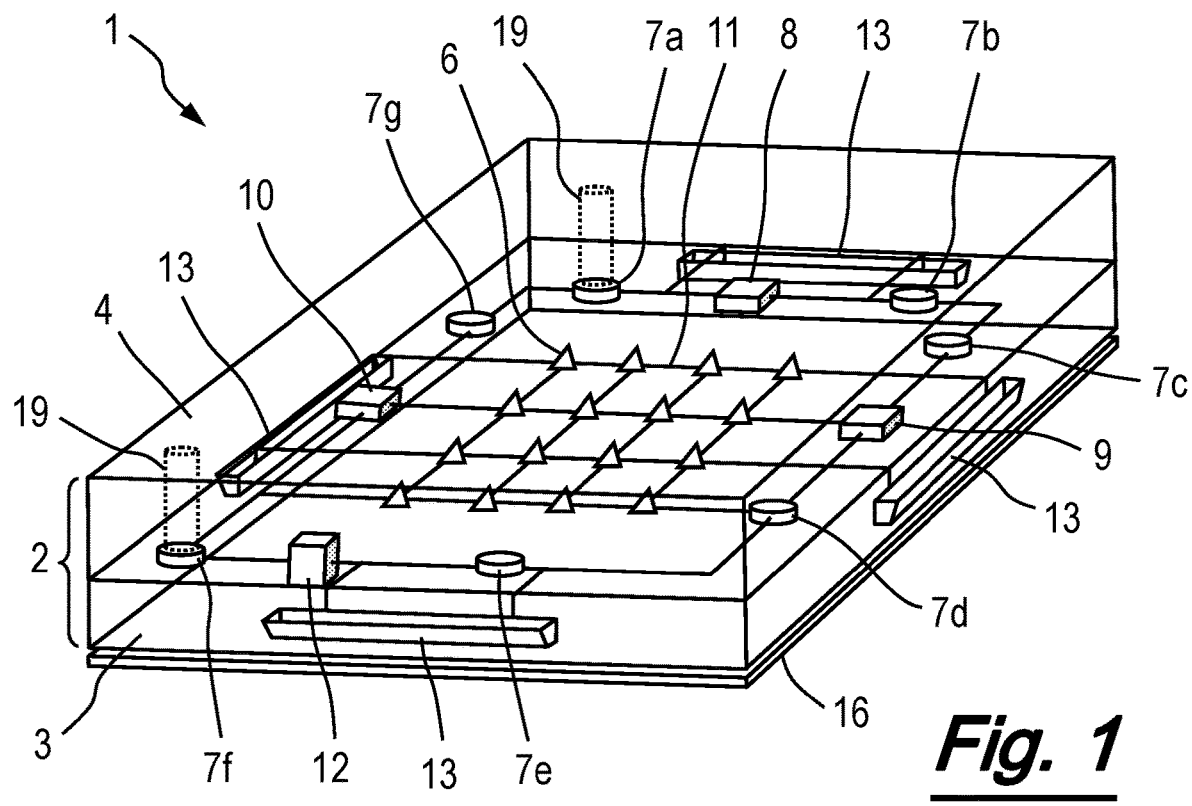
FIG. 1 presents a perspective view of a modular lighting panel in accordance with an embodiment of the present invention.

In the description which follows, like parts are marked throughout the specification and drawings with the same reference numerals. The drawings are not necessarily to scale and the proportions of certain parts have been exaggerated to better illustrate details and features of embodiments of the invention.

DETAILED DESCRIPTION OF PREFERRED EMBODIMENTS

Figure 2:
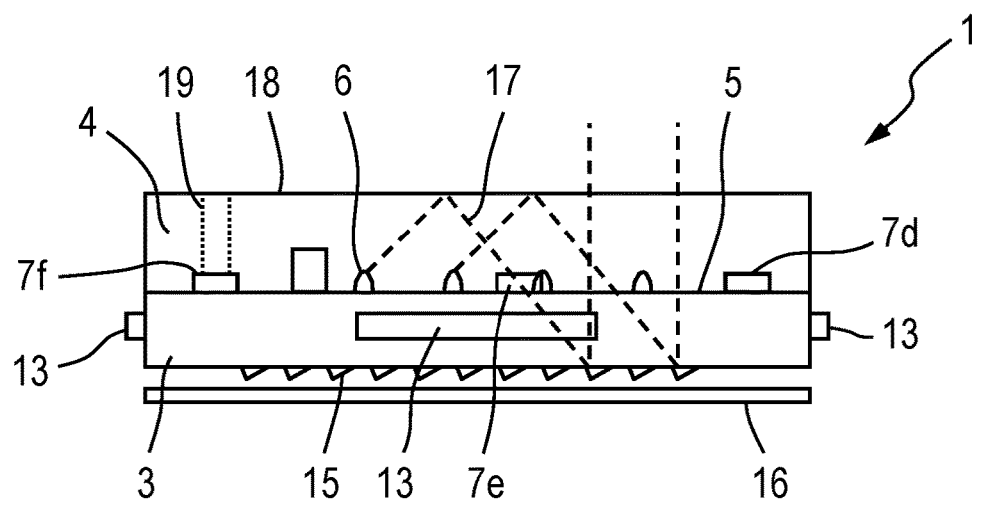
FIG. 2 presents a side view of the modular lighting panel of FIG. 1.

An explanation of the present invention will now be described with reference to FIGS. 1 and 2. In particular, FIG. 1 presents a perspective view of a modular lighting panel 1 in accordance with an embodiment of the present invention, while FIG. 2 presents a side view of the modular lighting panel 1.

The modular lighting panel 1 can be seen to comprise a composite light guiding structure 2 formed from a transparent base substrate 3, made from a transparent polymer sheet such as polyester or polycarbonate and having a refractive index $n_b$ between 1.50 and 1.58 and a transparent protecting layer 4, also formed from a plastic polymer and having a refractive index $n_p$ between 1.46 and 1.56.

On a first surface 5 of the transparent base substrate 2 is bonded an array of light sources 6, the light sources 6 preferably being in the form of LEDs. The array of light sources 6 is preferably located centrally on the first surface 5. The light sources 6 may emit light within a common wavelength region i.e. effectively be of the same colour. Alternatively, the light sources 6 may emit light within a different wavelength region i.e. effectively be of different colours. In this embodiment, the modular lighting panel 1 is able to control and change its output colour.

Located around the perimeter of the array of light sources 6 are a number of environment sensor units 7. In particular, the environment sensor units may comprise one or more of the following:

1) a thermometer 7a arranged to measure the ambient temperature of the volume illuminated by the array of light sources 6;

2) a photodetector 7b arranged to measure the ambient light levels of the volume illuminated by the array of light sources 6;

3) a pressure sensor 7c arranged to measure the ambient pressure of the volume illuminated by the array of light sources 6;

4) a hygrometer 7d arranged to measure the ambient humidity of the volume illuminated by the array of light sources 6;

5) a smoke detector 7e arranged to detect the presence of smoke within the volume illuminated by the array of light sources 6;

6) a carbon monoxide detector 7f arranged to detect the presence of carbon monoxide within the volume illuminated by the array of light sources 6; and 7) a carbon dioxide detector 7g arranged to detect the presence of carbon dioxide within the volume illuminated by the array of light sources 6.

It will be appreciated by the skilled reader that the environment sensor units may further comprise a gas detector suitable for detecting any predetermined gas within the volume illuminated by the array of light sources 6.

It will be appreciated by the skilled reader that not all of the above described environment sensor units 7 need be included within each modular lighting panel 1 and that different modular lighting panels 1 may comprise different combinations of these sensor units 7.

In addition to the above described light sources 6 and environment sensor units 7, the modular lighting panel 1 may comprise a number of additional components located on the first surface 5. For example, the modular lighting panel 1 may further comprise a motion sensor 8 (e.g. a passive infrared sensor) employed to detect movement within the volume illuminated by the array of light sources 6. In this way the array of lights can be automatically turned on when movement is detected within the volume illuminated by the array of light sources 6. The motion sensor 8 may comprise an image capture device (e.g. a camera) arranged to monitor the volume illuminated by the array of one or more light sources.

The modular lighting panel 1 may also comprise a wireless communication module 9 that provided a means for automated control of the functionality of the of one or more devices connected to the modular light panel. The wireless communication module 9 may provide a means for configuring the modular lighting panel 1 to communicate with the Internet of Things (IoT). This allows the modular lighting panel 1 to be connected to the outside world and thus provide a means for the generation of environmental data to facilitate an external intervention. The wireless communication module 9 may comprise a WiFi, LiFi or Bluetooth communication module. The wireless communication module may comprise an inductive antenna.

The one or more devices connected to the modular light panel may comprises the one or more environment sensor units 7 located on the first surface 5, although it will be appreciated that the one or more devices may comprise one or more devices located externally of the modular light panel e.g. a room thermostat.

A computer processing unit (CPU) 10 is preferably also mounted on the first surface 5 so as to provide a means for automatically controlling the other components of the modular lighting panel 1. The CPU 10 may be employed as a thermostat controller so as to provide a means for regulating the temperature within the volume illuminated by the array of light sources 6.

Electrical tracking 11 printed on the first surface 5 provides a means for supply power to the light sources 6, the environment sensor units 7, the motion sensor 8, the wireless communication module 9 and the CPU 10. Power may be provided by a dedicated power source 12 located within the modular lighting panel 1. Preferably however, the electrical tracking electrically connects the components of the modular lighting panel 1 to one or more connecting means 13 located around the perimeter of the transparent base substrate 3. The connecting means 13 are equivalent such that there is no dedicated input or output connecting means. In this way, multiple modular lighting panels 1 can be joined universally, by any of the connecting means 13 so as to provide a highly flexible lighting system. The lighting system can then be powered by an external power source e.g. mains power.

Located on a second surface 14 of the transparent base substrate 3 (i.e. that surface opposite to the first surface 5) is a scattering structure 15 in the form a patterned, reflecting ink layer. A reflective layer 16 may also be formed behind the second surface 14 so as to assist in directing light 17 generated by the light sources 6 towards the first surface 5.

The transparent protecting layer 4 is arranged to substantially cover the first surface 5 of the transparent base substrate 3 and encapsulate the components located thereon. In this way the transparent protecting layer 4 provides physical protection for the components located the first surface 5. An outer surface 18 of transparent protecting layer 4 defines the light exit surface for the modular lighting panel 1.

The refractive indices of the transparent base substrate 3 and the transparent protecting layer 4 are selected such that they satisfy the inequality:

$$n_b \geq n_p \quad (1)$$

As a result, and as can be seen from FIG. 2, light 17 generated by the light sources 6 is initially coupled into the transparent protecting layer 4 so as to propagate laterally across the device i.e. in a direction substantially perpendicular to the light exit surface 18. However, since the refractive index of the transparent base substrate 3 is selected to be equal to or higher than that of the transparent protecting layer 4, the generated light 17 is guided within both the transparent base substrate 3 and the transparent protecting layer 4 due to the effects of total internal reflection. Therefore, the transparent base substrate 3 and the transparent protecting layer 4 can be seen to form the composite structure 2 that acts as the guiding medium for the light 17 generated by the encapsulated LED light source 6.

When the light 17 has propagated as far as the scattering structure 15 it interacts with this structure so as to be redirected and so exit the device via the light exit surface 18, thus providing the desired lighting function. It will be readily apparent to those skilled in the art that the scattering structure 15 may alternatively be located on the outer surface 18 of the transparent protecting layer 4. In this embodiment, the redirected light will exit the device via the second surface 14 of the transparent base substrate 3.

It has been found advantageous for the operation of the environment sensor units 7 if an aperture 19 is formed within the transparent protecting layer 4 that provides a means for fluid communication to take place between the environment sensor units 7 and the volume illuminated by the array of light sources 6. The advantage of the presence of these apertures 19 is found to outweigh the detrimental impact that they have on uniformity of the light output from device.

Figure 3:
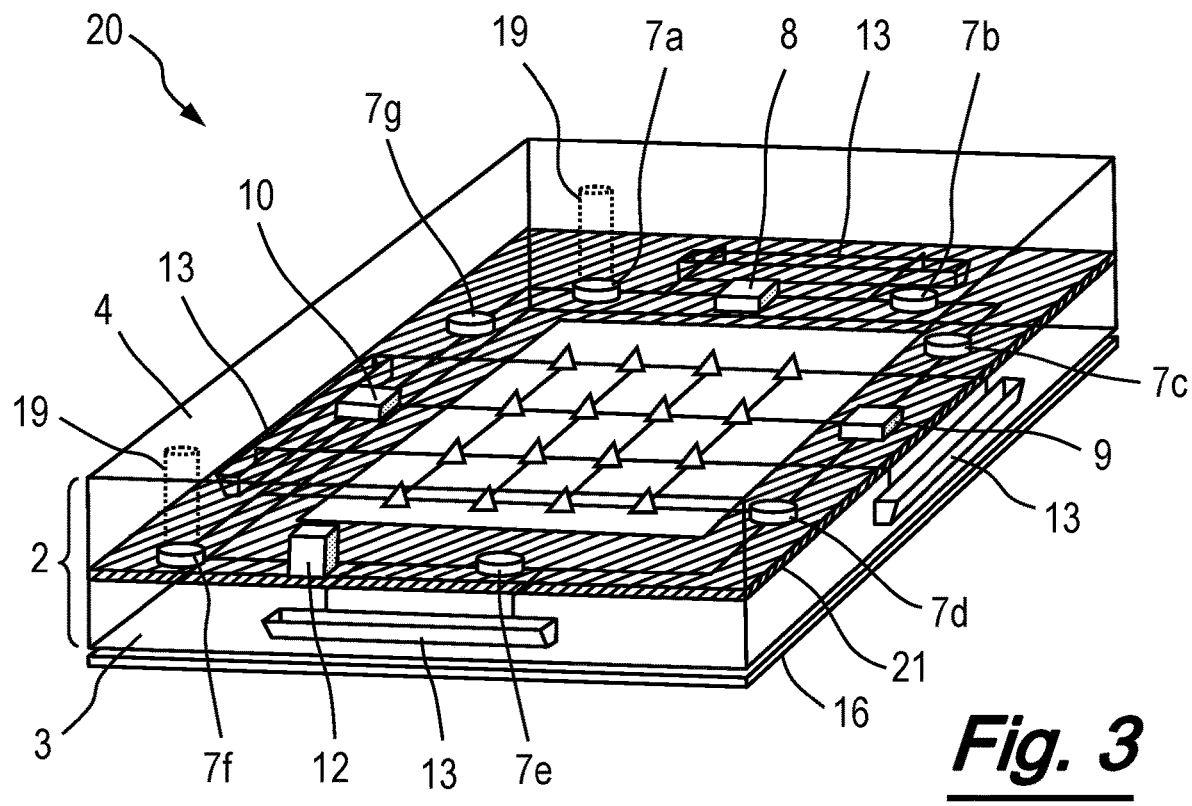
FIG. 3 presents a perspective view of an alternative embodiment of the modular lighting panel.

An explanation of an alternative embodiment of the present invention will now be described with reference to FIGS. 3 and 4. In particular, FIG. 3 presents a perspective view of a modular lighting panel 20 in accordance with this alternative embodiment, while FIG. 2 presents a side view of the modular lighting panel 20. The modular lighting panel 20 shares many components in common with the above described modular lighting panel 1 and so like parts are marked within FIGS. 3 and 4 with the same reference numerals.

Figure 4:
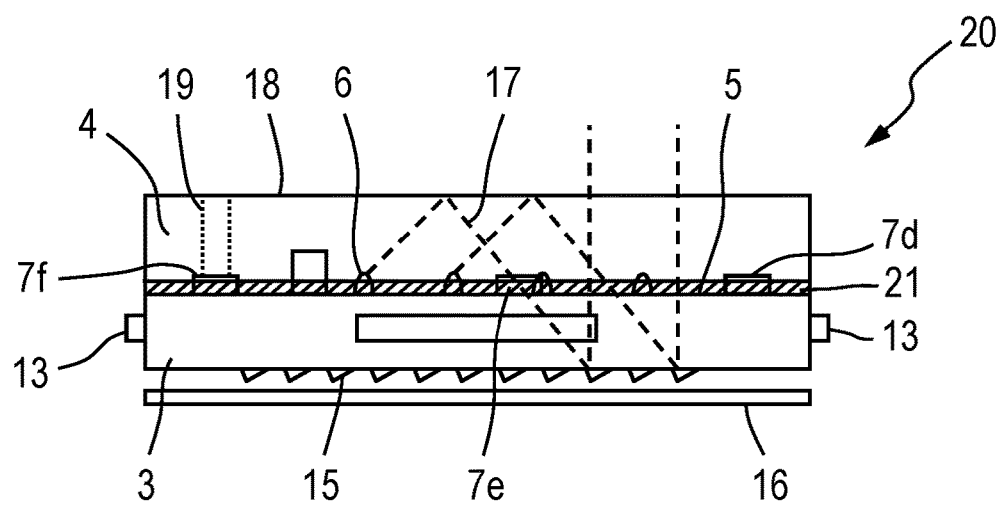
FIG. 4 presents a side view of the modular lighting panel of FIG. 3.

The main difference between modular lighting panel 1 of FIGS. 1 and 2 and that presently described with reference to FIGS. 3 and 4 is that the environment sensor units 7a to 7g incorporated therein are provided within a preformed organic layer 21. In particular, the environment sensor units 7a to 7g are formed from the deposition of organic sensor layers on top of transparent thin-film transistors all of which are mounted on a support layer formed from glass or plastic. In the presently described embodiment the support layer comprises a transparent polymer sheet such as polyester or polycarbonate and having a refractive index $n_o$. Since the light sources 6 are arrange to sit proud of organic layer 21 the refractive index $n_o$ of the organic layer is preferably chosen such that the following inequality is satisfied:

$$n_b \geq n_o \geq n_p \quad (2)$$

In this way, light 17 generated by the light sources 6 is initially coupled into the transparent protecting layer 4 so as to propagate laterally across the device. However, since the refractive indices of the transparent base substrate 3, the organic layer 21 and the transparent protecting layer 4 satisfy inequality (2) the generated light 17 can propagate through the organic layer 21 and into the transparent base substrate 3. Therefore, the transparent base substrate 3, the organic layer 21 and the transparent protecting layer 4 all form part of the composite structure 2 that acts as the guiding medium for the light 17 generated by the encapsulated LED light source 6.

The advantage of providing the environment sensor units 7a to 7g on the organic layer 21 is that it simplifies the manufacture process since all of these sensor units are provided within a single preformed component. In alternative embodiments, the functionality of the organic layer 21 may be further extended so as to incorporate one or more of the other components of the device e.g. the light sources 6, the motion sensor 8, the wireless communication module 9 and the CPU 10.

Figure 5:
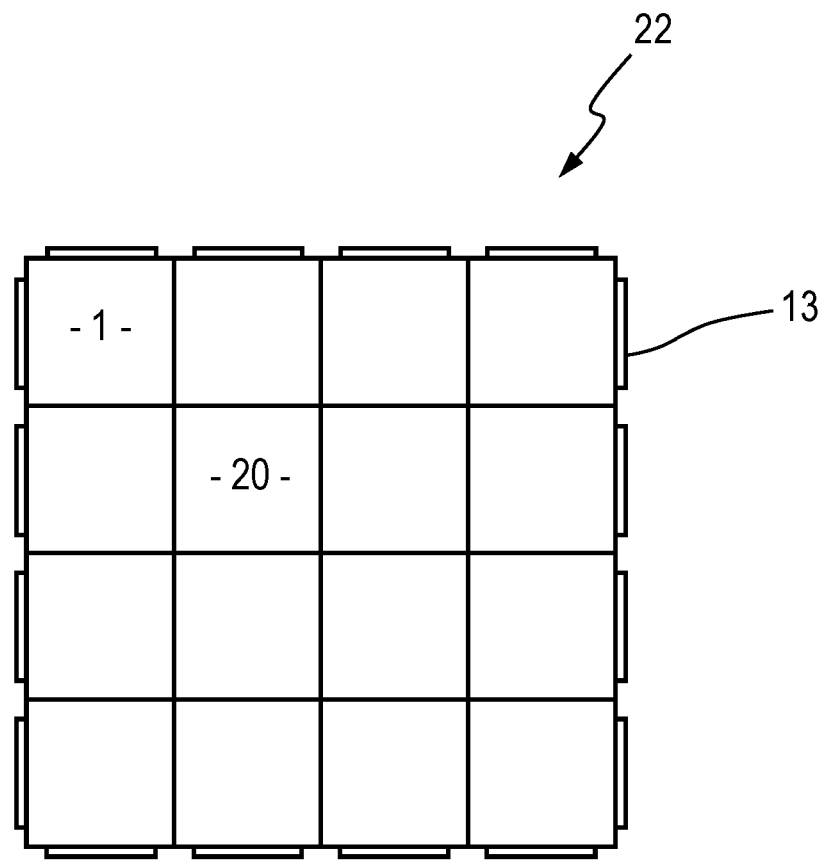
FIG. 5 presents a schematic representation of multiple modular lighting panels of FIG. 1 connected so as to form a roof lighting system.

A particular application of the modular lighting panels 1 and 20 can be seen with reference to FIG. 5. Here an array of sixteen modular lighting panels 1 and 20 has been formed so as to provide a light panel 22. The light panel may be employed as a wall or ceiling section for a room. Employing the light panel 22 as a roof section has the advantage that separate dedicated environment sensor units no longer need to be deployed within the volume of the room i.e. there is no need for a separate thermometer, photodetector, pressure sensor, hygrometer, smoke detector, carbon monoxide detector or carbon dioxide detector arranged to monitor the volume illuminated by the light panel 22. It will be recognised that if all of these environment sensor units 7 were incorporated within a single modular lighting panel 1 and 20 then this functionally could be achieved with a single modular lighting panels 1 and 20.

The above described light panel 22 when employed as a ceiling section for a room may provide a means for thermally mapping the temperature of the room. For example, the colour output from a particular modular lighting panels 1 and 20 can be correlated to the temperature measured by thermometer 7a located therein. In this way a spectrum of colours from blue to red may be employed to indicate the temperature of particular volumes of the room. For a volume appearing to be overheating an alarm could be activated and or a cooling apparatus activated. This functionality would find particular application for thermally mapping, and controlling, the temperature with a computer server room.

Figure 6:
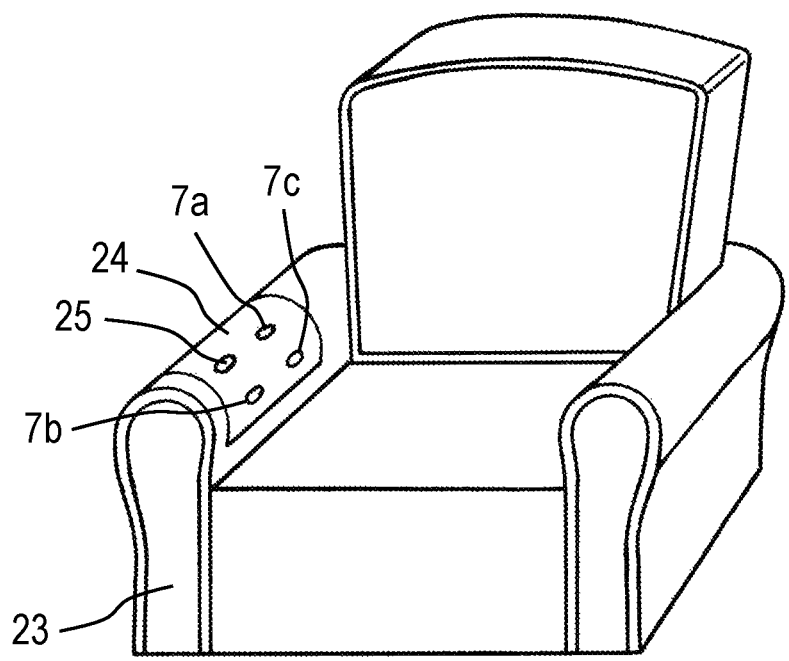
FIG. 6 presents a schematic representation of a modular lighting panel incorporated within the arm rest of a chair.

The flexible nature of the modular lighting panels 1 and 20 means that they can also be employed within an arm rest 23 of a chair, as presented schematically in FIG. 6. In this embodiment, the modular lighting panel 24 may further comprise a pulse measuring meter 25. The modular lighting panel 24 thus provide a means for detecting whether a person is sitting in the seat e.g. by employing the photodetector 7b or pressure sensor 7c while allowing for monitoring of the temperature and pulse of that person. This embodiment has particular application for the elderly where an alarm could be activated if their temperature or pulse drops below a predestined value.

An alternative application of the modular lighting panels 1 and 20 may be as a means for monitoring the internal volume of a manufacturing environment (e.g. a machine) where it would obviously be beneficial to be able to illuminate and monitor the internal environmental conditions and report these findings to an external system.

A further alternative application of the modular lighting panels 1 and 20 may be within the horticulture industry where the devices form part of the structure of a light tank or growth enhancing intelligent light system.

The modular light panels described above exhibits increased levels of light output when compared to those known in the art based on PCBs. They are also easier to manufacture while offering increased functionality. Employing the described modular light panels within a room removes the need for separate dedicated environment sensor units. By assembling an array of multiple modular light panels, they provide a means for thermally mapping the room.

A modular light panel is described that comprises a transparent base substrate, upon a first surface of which is mounted an array of light sources, and a transparent protecting layer arranged to encapsulate the light sources upon the first surface. The refractive index of these layers is such that they form a composite structure for guiding light produced by the light sources within the composite structure. The modular light panel also comprise a wireless communication module and or environment sensor units located on the first surface to measure one or more physical properties of a volume illuminated by the light sources. The modular light panel exhibits increased levels of light output, are easier to manufacture than known devices while offering increased functionality. In addition, they remove the need for separate dedicated environment sensor units to be employed in a room within which they are deployed while providing a means for thermally mapping the room.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

Furthermore, reference to any prior art in the description should not be taken as an indication that the prior art forms part of the common general knowledge.

The foregoing description of the invention has been presented for purposes of illustration and description and is not intended to be exhaustive or to limit the invention to the precise form disclosed. The described embodiments were chosen and described in order to best explain the principles of the invention and its practical application to thereby enable others skilled in the art to best utilise the invention in various embodiments and with various modifications as are suited to the particular use contemplated. Therefore, further modifications or improvements may be incorporated without departing from the scope of the invention as defined by the appended claims.

The invention claimed is:

1. A modular light panel comprising:
a transparent base substrate having a first refractive index;
an array of one or more light sources mounted on a first surface of the transparent base substrate;
a transparent protecting layer, having a second refractive index that is less than or equal to the first refractive index encapsulating the array of one or more light sources and forming a composite structure with the transparent base substrate for guiding light produced by the one or more light sources within the composite structure;
one or more environment sensor units mounted on the first surface and configured to measure one or more physical properties of a volume intended to be illuminated by the array of one or more light sources; and
a computer processing unit (CPU) that provides a means for automatically controlling one or more of the other components of the modular lighting panel.

2. A modular light panel as claimed in claim 1 wherein the array of one or more light sources is located centrally upon the first surface.

3. A modular light panel as claimed in claim 1 wherein the one or more environment sensor units are located around the perimeter of the array of one or more light sources.

4. A modular light panel as claimed in claim 1 wherein the one or more environment sensor units comprise a thermometer arranged to measure the ambient temperature of the volume intended to be illuminated by the array of one or more light sources.

5. A modular light panel as claimed in claim 1 wherein the one or more environment sensor units comprise a photodetector arranged to measure the ambient light levels of the volume intended to be illuminated by the array of one or more light sources.

6. A modular light panel as claimed in claim 1 wherein the one or more environment sensor units comprise a pressure sensor arranged to measure the ambient pressure of the volume intended to be illuminated by the array of one or more light sources.

7. A modular light panel as claimed in claim 1 wherein the one or more environment sensor units comprise a hygrometer arranged to measure the ambient humidity of the volume intended to be illuminated by the array of one or more light sources.

8. A modular light panel as claimed in claim 1 wherein the one or more environment sensor units comprise a smoke detector arranged to detect the presence of smoke within the volume intended to be illuminated by the array of one or more light sources.

9. A modular light panel as claimed in claim 1 wherein the one or more environment sensor units comprise a gas detector arranged to detect the presence of one or more gases within the volume intended to be illuminated by the array of one or more light sources.

10. A modular light panel as claimed in claim 1 wherein the CPU is mounted upon the first surface.

11. A modular light panel as claimed in claim 1 wherein the modular lighting panel further comprises a power source located within the modular lighting panel.

12. A method of thermally mapping the temperature of the room, the method comprising deploying two or more modular lighting panels as claimed in claim 1 within a ceiling area of the room.

13. A modular light panel as claimed in claim 1 wherein the transparent protecting layer also encapsulates the one or more environment sensor units upon the first surface.

14. A modular light panel as claimed in claim 13 wherein one or more apertures are located within the transparent protecting layer to provide a means for fluid communication between the one or more environment sensor units and the volume intended to be illuminated by the array of one or more light sources.

15. A modular light panel as claimed in claim 1 wherein the modular lighting panel further comprises a motion sensor that provides a means for detecting movement within the volume intended to be illuminated by the array of one or more light sources.

16. A modular light panel as claimed in claim 15 wherein the motion sensor is mounted upon the first surface.

17. A modular light panel as claimed in claim 1 wherein the modular lighting panel further comprises an image capture device that provides a means for imaging the volume intended to be illuminated by the array of one or more light sources.

18. A modular light panel as claimed in claim 17 wherein the image capture device is mounted upon the first surface.

19. A modular light panel as claimed in claim 1 wherein the modular lighting panel further comprises a wireless communication module that provided a means for automated control of the functionality of the device.

20. A modular light panel as claimed in claim 19 wherein the wireless communication module is mounted upon the first surface.

21. A modular light panel as claimed in claim 1 wherein the modular lighting panel further comprises a thermostat controller to provide a means for regulating the temperature within the volume intended to be illuminated by the array of one or more light sources.

22. A modular light panel as claimed in claim 21 wherein the CPU is employed as the thermostat controller.

23. A light panel comprising two or more modular lighting panels as claimed in claim 1.

24. A light panel as claimed in claim 23 wherein the light panel forms a ceiling section of a room.

25. An arm rest for a chair comprising a modular lighting panel as claimed in claim 1.

26. An arm rest as claimed in claim 25 wherein the modular lighting panel further comprises a pulse measuring meter.

27. A modular light panel as claimed in claim 1 wherein the one or more environment sensor units are formed on an organic layer.

28. A modular light panel as claimed in claim 27 wherein the organic layer comprises a transparent polymer sheet having a refractive index no.

29. A modular light panel as claimed in claim 27 wherein the array of one or more light sources are also formed on the organic layer.

30. A modular light panel as claimed in claim 27 wherein the modular lighting panel further comprises:
a motion sensor that provides a means for detecting movement within the volume intended to be illuminated by the array of one or more light sources; and
a wireless communication module that provides a means for automated control of the functionality of the device;
wherein the motion sensor, the wireless communication module and the CPU are formed on the organic layer.

31. A modular light panel as claimed in claim 1 wherein the modular lighting panel further comprises one or more scattering structures arranged to direct light generated by the array of one or more light sources towards an exit surface of the modular lighting panel.

32. A modular light panel as claimed in claim 31 wherein the one or more scattering structures are located on a second surface of the transparent base substrate, the second surface being opposite to the first surface.

33. A modular light panel as claimed in claim 32 wherein the modular lighting panel further comprises a reflective layer formed behind the second surface to assist in directing light generated by the array of one or more light sources towards the exit surface of the modular lighting panel.

34. A modular light panel as claimed in claim 1 wherein the modular lighting panel further comprises electrical tracking located on the first surface that provides a means for supplying power to the array of one or more light sources and the one or more environment sensor units.

35. A modular light panel as claimed in claim 34 wherein the modular lighting panel further comprises a motion sensor that provides a means for detecting movement within the volume intended to be illuminated by the array of one or more light sources, and wherein the electrical tracking provides a means for supplying power to the motion sensor.

36. A modular light panel as claimed in claim 34 wherein the modular lighting panel further comprises a wireless communication module that provides a means for automated control of the functionality of the device, and wherein the electrical tracking provides a means for supplying power to the wireless communication module.

37. A modular light panel as claimed in claim 34 wherein the electrical tracking provides a means for supplying power to the CPU.

38. A modular light panel as claimed in claim 34 wherein the electrical tracking is electrically connected to one or more connecting means located around the perimeter of the modular lighting panel.

39. A modular light panel as claimed in claim 38 wherein the connecting means are connected to an external power source.

* * * * *